United States Patent [19]

Pelley

[11] Patent Number: 5,213,817
[45] Date of Patent: May 25, 1993

[54] APPARATUS FOR INTERMITTENTLY APPLYING PARTICULATE POWDER MATERIAL TO A FIBROUS SUBSTRATE

[75] Inventor: Kenneth A. Pelley, Hopewell, N.J.

[73] Assignee: McNeil-PPC, Inc., Milltown, N.J.

[21] Appl. No.: 806,954

[22] Filed: Dec. 12, 1991

[51] Int. Cl.⁵ ............................ B05B 12/06; B05C 1/16
[52] U.S. Cl. ................................. 425/81.1; 118/308;
 239/124; 264/510; 264/131; 425/145; 425/166;
 425/217; 425/375; 425/83.1
[58] Field of Search ................. 118/308, 312; 239/97,
 239/99, 124, 380; 264/113, 510, 511, 518, 131;
 425/80.1, 81.1, 83.1, 115, 145, 155, 166, 217,
 220, 375, 447; 156/62.2, 62.6, 167; 222/424;
 427/197, 200

[56] References Cited

U.S. PATENT DOCUMENTS

| | | | |
|---|---|---|---|
| 3,187,386 | 6/1965 | Schubert et al. | 425/83.1 |
| 4,138,161 | 2/1979 | Payne | 239/124 |
| 4,675,209 | 6/1987 | Pedigrew | 427/197 |
| 4,770,344 | 9/1988 | Kaiser | 239/8 |
| 4,800,102 | 1/1989 | Takada | 427/197 |
| 4,861,405 | 8/1989 | Kassai | 156/276 |
| 4,882,204 | 11/1989 | Tenenbaum | 427/180 |
| 4,921,650 | 5/1990 | Eriksson et al. | 425/217 |
| 4,927,346 | 5/1990 | Kaiser et al. | 425/81.1 |
| 4,927,582 | 5/1990 | Bryson | 425/81.1 |
| 5,028,224 | 7/1991 | Pieper et al. | 264/113 |

FOREIGN PATENT DOCUMENTS 9118137 11/1991 Norway .................... 425/81.1

Primary Examiner—Scott Bushey

[57] ABSTRACT

An apparatus for applying particulate powder material to a moving fibrous substrate is disclosed. The apparatus includes a volumetric dry material feeder for forming a continuous stream of particulate powder material. The continuous stream is then transmitted through a nozzle and exits at an outlet thereof. The nozzle is movable between a first and second position by a motion control. The motion control includes an adjustable differential gear box and an encoder for synchronizing the dispensing of powder at a predetermined location of the substrate. A flow separator is disposed beyond the outlet of the nozzle and intermediate of the first and second positions. In operation, the motion input drives the nozzle to oscillate between the first and second positions at a variable speed over each product cycle. As the nozzle crosses a plane of the flow separator, the continuous stream of particulate powder material exiting the nozzle is split into two intermittent streams of particulate powder material. The first intermittent stream is applied to a predetermined location of the moving fibrous substrate to form a layer of particulate powder material within a predetermined portion of the substrate. The second intermittent stream is recirculated back to the volumetric dry material feeder.

13 Claims, 3 Drawing Sheets

APPARATUS FOR INTERMITTENTLY APPLYING PARTICULATE POWDER MATERIAL TO A FIBROUS SUBSTRATE

BACKGROUND OF THE INVENTION

1. Field of the Invention

The present invention relates to a method and apparatus for fabricating a fibrous pad containing a layer of powder therein, and more particularly, to a method and apparatus for intermittently spraying particulate powder material onto predetermined locations of a moving fibrous substrate to form a layer of particulate powder material within a predetermined portion of the fibrous substrate.

2. Description of the Prior Art

Hygenic articles such as disposable diapers, sanitary napkins, incontinence pads and sick bed sheets must have a high absorption capacity to effectively retain eliminated body fluids for acceptable periods of time. Early hygenic articles of this type employed cellulose wadding, fluff cellulose or absorbent cotton as absorbent materials. The problem with these materials is that their absorbent capacity is relatively small compared to their volume. In order to improve the moisture retaining capacity of hygenic articles made from these materials, the volume of such absorbent materials in the hygenic article must be increased. This produces a bulky product which is unacceptable in many hygenic articles, particularly sanitary napkins.

To reduce the volume and size of hygenic articles, and increase their absorbent capacity, highly absorbent materials have been developed and are combined within a fluid absorbent fibrous substrate composed of cellulose fluff, wood pulp, textile fibers or other non-woven, fibrous materials. Such highly absorbent materials which have a high capacity for absorbing water and body fluids are known in the art and generally consist of water insoluble, water-resisting organic polymers. These polymers are partially or wholly synthetic and are commercially available in fine grain, particulate form.

Various techniques have been developed to distribute and locate the highly absorbent material on or within the fibrous substrate. One prior art method of combining powder with a fibrous substrate comprises applying the powder to a top surface of the substrate. For example, U.S. Pat. No. 4,800,102 discloses a method and apparatus for spraying powder onto a fibrous substrate through a rotatable disc member having at least one opening through which powders continuously sprayed from a spraying means can reach the substrate. The apparatus also includes scraper means disposed above and closely adjacent to the disc member for deflecting powder from the surface of the disc member through an opening. A lower powder receiving member is disposed beneath the scraper means for collecting powder material deflected by the scraper means. An upper powder sucker is disposed above the disc member adjacent the scraper means and is effective to remove from the disc member any powder which is not forced by the scraper means through the opening. The powder material recovered by the lower powder member and the upper sucker are transported back to a powder supply. U.S. Pat. No. 4,861,405 also discloses a method and apparatus for spraying powder to a top surface of a laminated continuous sheet. The system of this patent utilizes the speed of the continuous sheet to create an air flow zone of a predetermined thickness over a predetermined surface of the continuous sheet. Powder is continuously fed to the air zone by free fall through a conduit and by utilizing a decreasing-pressure phenomenon produced by the air flow in which the pressure decreases as the predetermined surface of the laminated continuous sheet is approached. Powder is caused to adhere to the predetermined surface as it is drawn toward the predetermined surface of the laminated continuous sheet.

Another prior art method disclosed in U.S. Pat. No. 4,882,204 utilizes an aerosol spray nozzle of an aerosol container having absorbent powder particles to form a diaper having highly absorbent material over the entire length and width of the diaper. The spray force drives many of the powder particles into subsurface layers of the diaper.

U.S. Pat. No. 4,675,209 discloses another prior art method for applying highly absorbent material onto a top surface of a moving substrate. This method includes the steps of dispensing a melt adhesive film on precisely defined areas of the substrate, covering such areas with the absorbent material and then removing excess material which did not adhere to the adhesive coated areas.

Another prior art method of combining moisture absorbent material with a fibrous substrate comprises intermixing highly moisture-absorbent material with fibrous material in a forming chamber. U.S. Pat. No. 4,927,346 discloses an apparatus for forming a non-woven pad consisting of fibrous material in which highly absorbent particles are intermixed with fibrous material throughout a predetermined portion of the thickness of the pad. The non-woven pad is formed on top of a conveyor moving through a chamber which has a duct connected to a vacuum source operable to draw fibrous material injected into the chamber onto the conveyor. A spray gun atop the conveyor discharges moisture absorbent material at a predetermined velocity, such that the moisture absorbent material is intermixed with the fibrous material throughout a center layer of the thickness of the non-woven pad while forming boundary layers on either side of the center layer which are substantially free of moisture absorbent material. The spray gun is operable intermittently to form spaced, sharply defined areas along the length and width of the non-woven pad wherein each area has moisture absorbent material interspersed throughout a portion of the thickness thereof.

The conventional devices described above have problems associated with loss of moisture absorbent material through the conveyor in the forming chamber. In addition, the prior art methods which produce a substrate having highly absorbent material throughout the entire length and/or width produces substantial waste because in subsequent forming operations the non-woven pad is cut to the desired length of the hygenic article. Prior art methods which produce a substrate having the absorbent material on a top surface have the disadvantage that the moisture absorbent capacity of the non-woven pad is substantially limited. This causes "gel blockage" wherein the moisture absorbent material at the top of the pad becomes saturated with fluid and prevents the transfer of moisture to the remaining portion of the pad. As a result, the fluid is retained at the surface of the pad in contact with the wearer of the hygenic article causing discomfort. Another disadvantage with these methods is that the moisture absorbent material is of a particulate or granular form and can be dislodged from the type of pads which are not sealed at the ends.

Product specifications for present hygenic articles require high absorbency material to be centrally located within a fibrous pad and it may not extend to the edges or ends of the pad. In addition, the absorbent material must be applied in a manner which does not damage or pass through the pad. Conventional devices and techniques, such as those discussed above, have not, however, been sufficiently capable of efficiently producing a fibrous pad having particulate powder material distributed in a predetermined portion of the thickness, and across the length and width, of the pad. In addition, the conventional forming techniques have not been sufficiently able to deliver powder materials in a substantially uniformly dispersed configuration that can be readily directed and distributed into predetermined locations and patterns within the fibrous pad.

SUMMARY OF THE INVENTION

The present invention is directed to a method and apparatus for applying particulate powder material to a moving fibrous substrate at predetermined locations to form a layer of particulate material within a predetermined thickness of the substrate and over a predetermined surface of the substrate. The apparatus of the present invention includes a source of supply for the particulate powder material. The particulate powder material is transferred from the supply source to a hopper of a volumetric dry material feeder. The volumetric feeder includes a metering screw and nozzle shroud at its outlet to discharge an accurately metered quantity of particulate powder material to the outlet of the volumetric feeder. Particulate powder material is then pneumatically conveyed to a nozzle. The continuous stream of particulate powder material flows through the nozzle and exits at an outlet thereof. The nozzle includes a stationary pivot mounted near its inlet and a movable pivot mounted near the center of the nozzle. The nozzle is movable at a variable speed between a first position and a second position about the stationary pivot. A flow separator is disposed intermediate of the first and second positions beyond the outlet of the nozzle. The motion of the nozzle is controlled by a cam type drive connected to the movable pivot.

The motion input to the cam type drive originates at a maker drive shaft which controls the rate of the moving fibrous substrate. An adjustable differential gear box is disposed between the maker drive shaft and an encoder to allow synchronizing the dispensing of the particulate powder material at a predetermined location of the substrate. The encoder is driven by a shaft of the gear box such that the encoder turns one revolution per product cycle. A programmable controller communicates with the output of the encoder and a servomotor. The servomotor is connected to the movable pivot of the nozzle by a cam shaft. The programmable controller drives the servomotor at a variable speed for each product cycle.

The motion input to the nozzle causes the nozzle to oscillate between first and second positions such that the continuous stream of particulate material exiting the nozzle outlet is split into a first and second intermittent stream as the nozzle crosses the axis of the flow separator. The first intermittent stream of particulate powder material is applied to the moving fibrous substrate at a predetermined rate and at a predetermined location to form a layer of particulate powder material within a predetermined portion of the thickness of the fibrous substrate.

In an alternative embodiment of the present invention, recycle means are provided to receive the second intermittent stream of particulate powder material and pneumatically return it to the hopper of the volumetric feeder. The recycle means includes a cyclone to separate the particulate powder material from process air. The particulate powder material is discharged from the cyclone through a rotary air lock and free falls back into the hopper of the volumetric feeder.

The method and apparatus of the present invention allows an accurately metered quantity of particulate powder material to be applied to a moving fibrous substrate in a more precise manner than prior art methods and apparatus. In addition, the use of recycle means lowers the amount of particulate powder material which is used for each product thereby leading to a lower raw material cost.

DETAILED DESCRIPTION OF THE INVENTION

Figure 1:
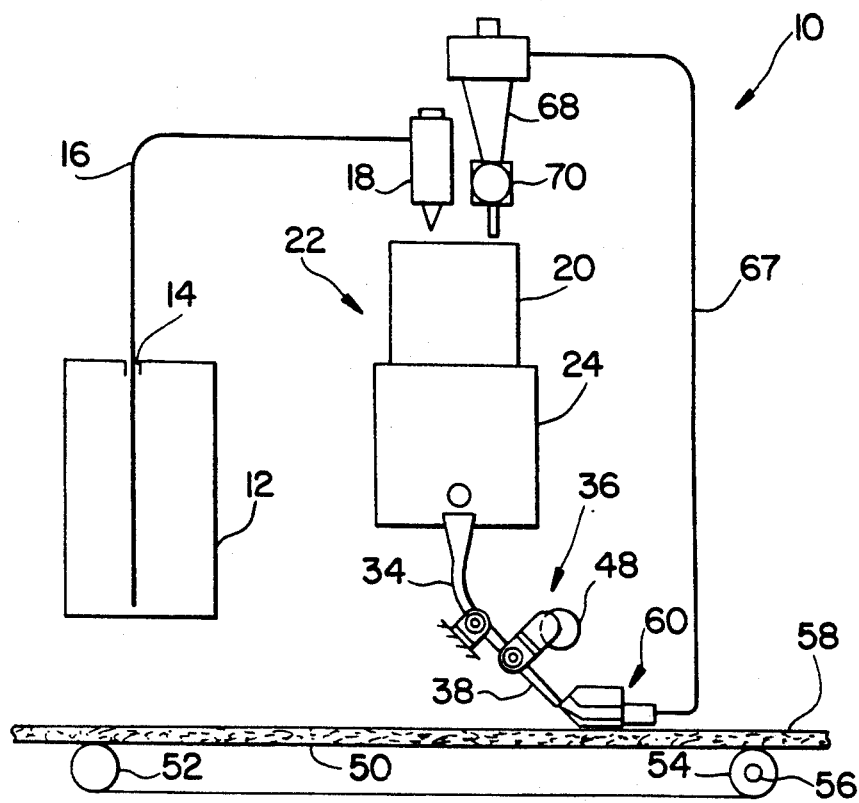
FIG. 1 is a schematic side view of the intermittent particulate powder material dispensing apparatus of the present invention.

Referring now to FIG. 1, an apparatus 10 for intermittently dispensing particulate powder material onto a moving fibrous substrate is illustrated. The apparatus 10 of the present invention can be used for particulate powder materials such as sodium biocarbonate, high absorbency polymers and other powders which are used in hygenic articles such as diapers, sanitary napkins and incontinence pads. The apparatus 10 includes a source of supply 12 for the particulate powder material. The source of supply 12 can be a storage drum or any other suitable container for storing particulate powder material. The source of supply 12 has an outlet 14 which is adapted to receive a tube 16. The tube 16 extends to the bottom of the source of supply. A drum unloader 18 is connected to the source of supply 12 through tube 16. The drum unloader 18 is a vacuum source and is operable to pneumatically transfer the particulate powder material from the supply source 12 to a dump hopper 20 of a volumetric dry material feeder 22. Automatic controls (not shown) on the drum unloader communicate with high and low sensors located within the dump hopper 20 and are operable to maintain the level of particulate powder material in the dump hopper 20 between the high and low sensors. This system for maintaining the level of particulate powder is conventional and well known in the art and any suitable system for maintaining said level may be employed.

Figure 2:
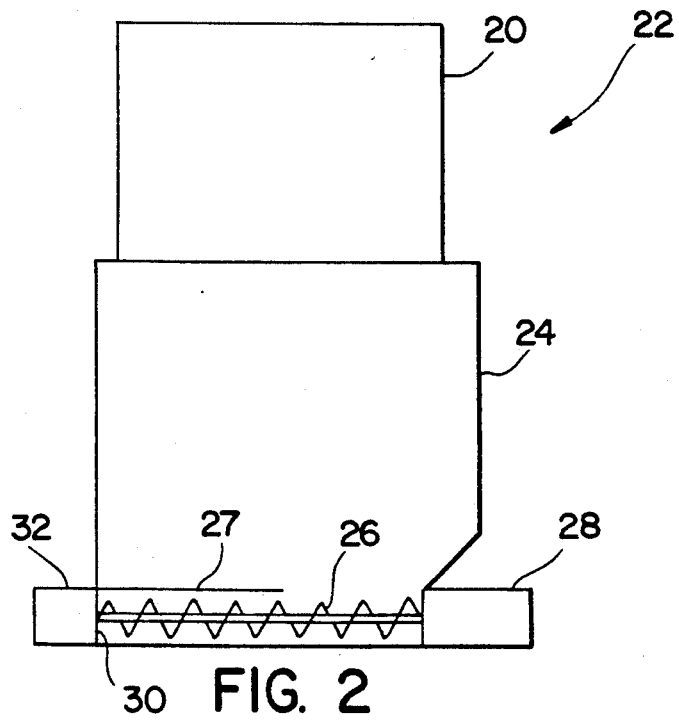
FIG. 2 is a schematic view of the volumetric feeder of the present invention.
Figure 3:
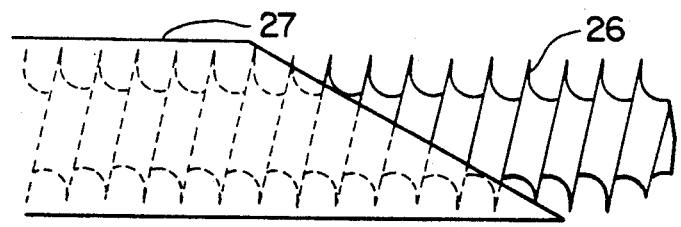
FIG. 3 is an elevational view of the metering screw and nozzle shroud of the volumetric feeder of the present invention.

Referring now to FIGS. 1, 2 and 3, the volumetric feeder 22 includes a feed hopper 24 located below the dump hopper 20. An example of a volumetric dry material feeder 22 which can be adapted to be used in the present invention is disclosed in U.S. Pat. No. 4,770,344 which is hereby incorporated by reference. The feeder 22 also includes external massaging paddles (not shown) to break bridges and condition the particulate powder material into a uniform bulk density. Mounted within the base of the feed hopper 24 is a metering screw 26 and nozzle shroud 27. The metering screw 26 is driven by a motor 28 at a predetermined rate. The metering screw 26 is rotatable to discharge an accurately metered quantity of particulate powder material from the feed hopper 24 through an outlet 30 formed within the base of feed hopper 24. The metering screw 26 and nozzle shroud 27 are designed to improve the instantaneous metering consistency of particulate powder material discharged through outlet 30. The outlet 30 is connected to a powder pump 32 which receives the accurately metered quantity of the particulate powder material and entrains it within a stream of air for transmittal through a flexible hose 34 connected to the outlet 30.

Figure 4:
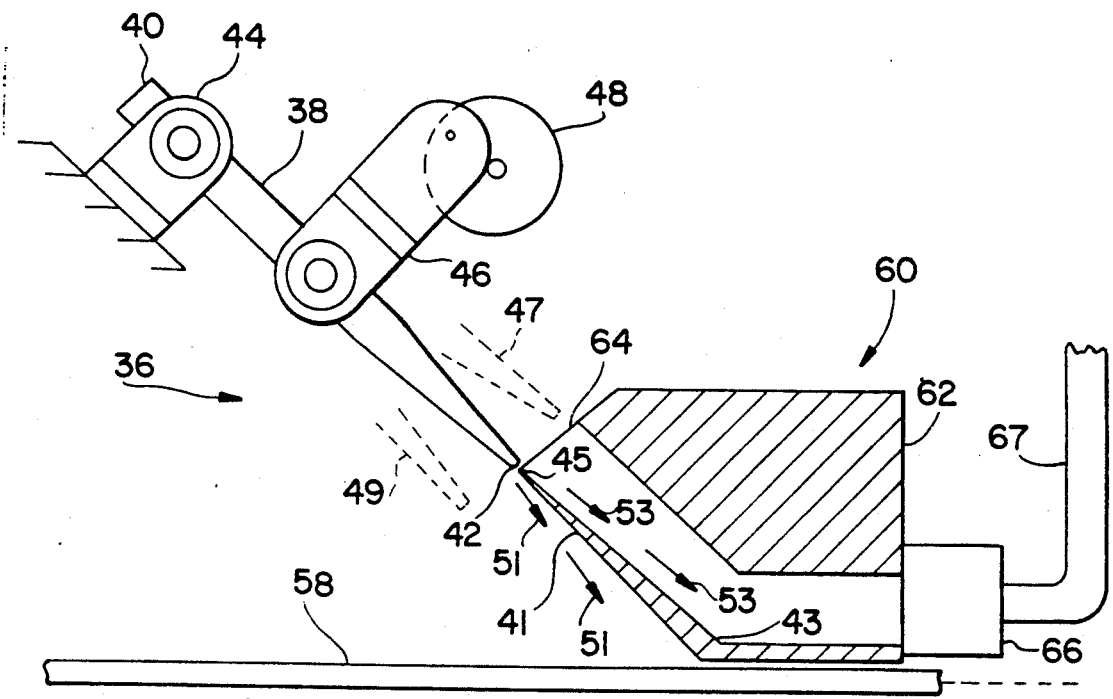
FIG. 4 is a schematic side view of the diverter nozzle and a cross-sectional side view of the diverter block of the present invention.

Turning now to FIG. 4, there is shown a diverter apparatus 36 which includes a nozzle 38 having an inlet 40 connected to the flexible hose 34 for receiving the continuous stream of air-entrained particulate powder material passing through hose 34. Nozzle 38 is a generally tubular shaped member having a hollow interior and tapers in an outlet 42 which has a rectangular cross-section (not shown). The continuous stream of particulate powder material flows through nozzle 38 and exits at outlet 42. The tapered shape of nozzle 38 and rectangular cross-section of outlet 42 combine to focus the shape of particulate powder material exiting outlet 42 into a concentrated and well-defined continuous stream of powder material. A knife edge flow separator 41 is disposed beyond the outlet 42 of nozzle 38. The flow separator 41 is wedge shaped having a wide end 43 and tapering to a narrow end 45. The flow separator has a rectangular cross-section taken along a view perpendicular to a plane of the separator 41. A stationary pivot 44 is mounted near the inlet 40. A cam shaft 46 is mounted near the center of nozzle 38. The cam shaft 46 is connected to a disc 48 near its outer edge. The nozzle 38 is movable between a first position 47 and a second position 49 by a motion control applied to the cam shaft 46. As the nozzle 38 oscillates between the first and second positions 47 and 49, the continuous stream exiting at outlet 42 will be diverted into two intermittent streams of particulate powder material each time the nozzle 38 crosses the plane of the flow separator 41. As an example of the formation of two intermittent streams in accordance with the method of the present invention, FIG. 4 shows a first intermittent stream of particulate powder material 51 and a second intermittent stream of particulate powder material 53 formed as nozzle 38 moves from 47 to 49 to 47 to 49 to the plane of flow separator 41.

Referring now to FIGS. 1 and 4, a conveyor 50 is located below the nozzle 38. The conveyor 50 is passed over cylindrical rollers 52 and 54, of which the driving roller 54 is driven by a motor (not shown) at a predetermined rate. The motor includes a drive shaft 56 which rotates at the predetermined rate. An elongated fibrous substrate 58 is placed on the conveyor and moves in the direction shown by the arrows. As will be described in more detail below, the first intermittent stream of particulate powder material 51 is applied to a predetermined location of the moving substrate 58.

In an alternative embodiment of the present invention, a recycle apparatus 60 can be utilized. The recycle apparatus 60 includes a diverter block 62 having a rectangular inlet 64 for receiving the second intermittent stream of particulate powder material 53. The cross-sectional length of the inlet 64 is preferably at least as long as the cross-sectional length of nozzle outlet 42 in order to allow the entire second intermittent stream 53 to flow into inlet 64. A pump 66 is used to pneumatically convey the second stream of particulate powder material 53 through a tube 67 to a cyclone 68. The cyclone 68 separates the particulate powder material from the process air used to convey the second stream of powder material. The particulate powder material is then discharged from cyclone 68 through a rotary air lock 70 and free falls back into the dump hopper 20 of the volumetric feeder 22.

Figure 5:
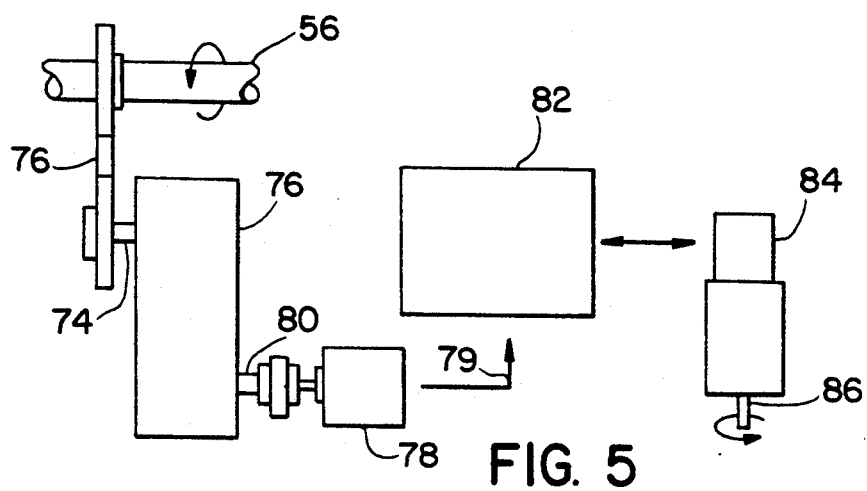
FIG. 5 is a schematic side view of the motion control for the diverter nozzle in accordance with the method and apparatus of the present invention.
Figure 6:
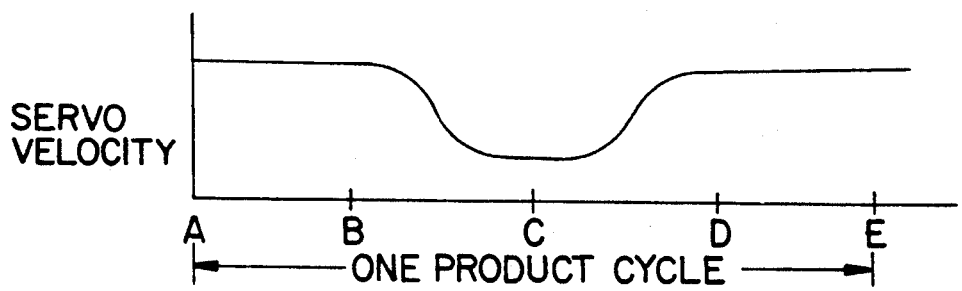
FIG. 6 is a graph of the servovelocity of the servomotor of the present invention for one product cycle.

Referring now to FIG. 5 there is shown a schematic diagram of the motion control for the diverter nozzle 38. The motion input to nozzle 38 originates at the maker drive shaft 56. The maker drive-shaft 56 is connected to an adjustable differential gear box 72 at a first shaft 74 by a belt 76. An encoder 78 is connected to the differential gear box 72 at a second shaft 80. The differential gear box 72 is adjustable such that the encoder 78 turns one revolution per product cycle. This allows synchronizing the dispensing of particulate powder material at a predetermined location of the fibrous substrate 58. The encoder 78 produces an output 79 which is received by a programmable controller 82. The controller 82 communicates with a servomotor 84 which has a shaft 86 connected to disc 48. The controller 82 drives the servomotor 84 such that its shaft 86 has a variable speed profile over one product cycle as shown in FIG. 6. In addition, the variable speed profile of servomotor 84 will cycle at the predetermined rate of the maker drive shaft 56.

In operation, conveyor 50 having the fibrous substrate 58 thereon is moving at a predetermined rate. At the same time, an accurately metered continuous stream of particulate powder material is being discharged through the outlet 42 of nozzle 38. The nozzle 38 is being moved between the first and second positions 47 and 49 according to the variable speed profile of servomotor 84 by cam shaft 46 and is cycling at the predetermined rate. As an illustrative example, the nozzle 38 may begin from first position 47, corresponding to position A of the variable speed profile of servomotor 84, and quickly reaches the narrow end 45 of the separator 41 corresponding to position B. Up to this point, particulate powder material flows into the inlet 64 of diverter block 62. As the nozzle 38 quickly crosses the plane of the separator 41 the motion of the nozzle 38 slows down due to the variable speed of servomotor 84, reaches the second position 49 corresponding to position C and begins to return to the narrow end 45 of separator 41 corresponding to position D. During this period, particulate powder material is applied to the fibrous substrate 58 at a predetermined location to form a layer of particulate powder material within a predetermined portion of the thickness of the fibrous subsrate 58. The nozzle 38 then quickly returns to its first position 47 corresponding to position E. For each product this cycle repeats itself. Typically, the present invention operates at 600 product cycles per minute.

The diverter nozzle 38 is preferably angled in the direction of movement of the fibrous substrate 58 to give the particulate powder material a velocity component in the same direction as the moving substrate 58 in order to reduce "splashing" of particulate powder material off the substrate 58. The wedge shaped separator combined with the fast motion of nozzle 38 when it crosses the plane of separator 41 produce a clean cut-off of particulate powder material flow each time the nozzle 38 crosses the plane of separator 41. This allows the diverter apparatus 36 to generate well defined first and second intermittent streams of particulate powder material.

Figure 7:
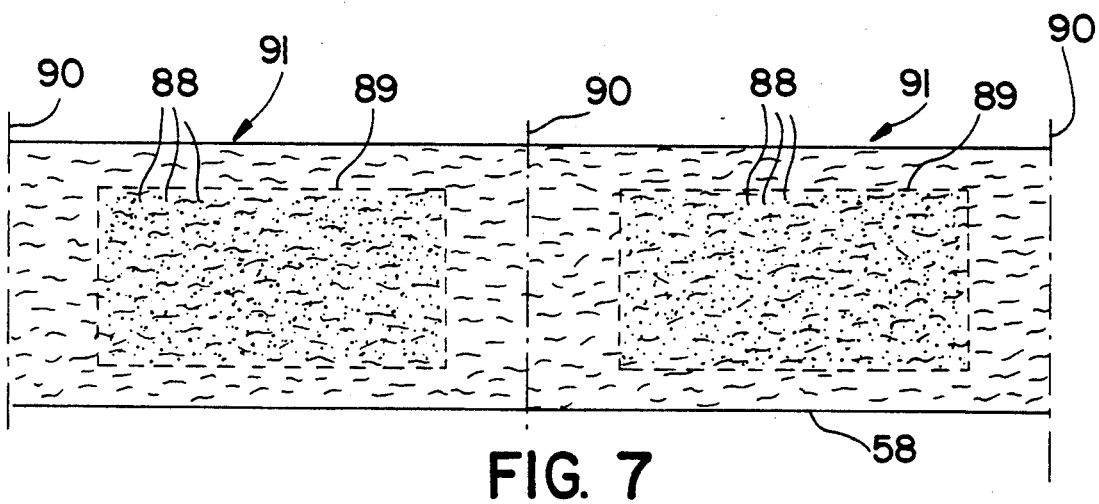
FIG. 7 is a top view of a fibrous substrate having particulate powder material at selected locations utilizing the method and apparatus of the present invention.
Figure 8:
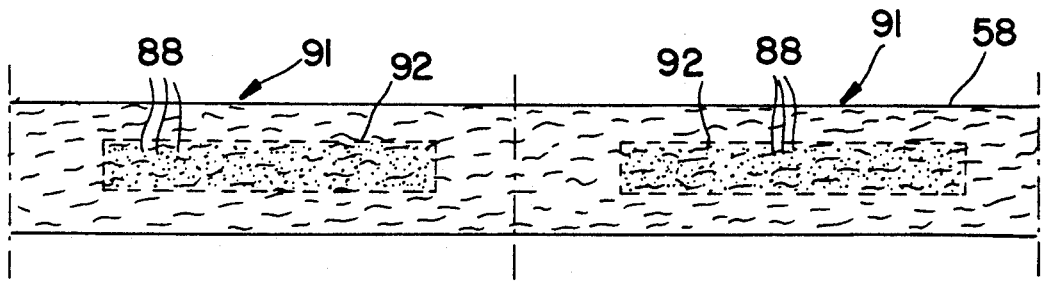
FIG. 8 is a cross-sectional view of the fibrous substrate of FIG. 4 having particulate powder material within a predetermined portion of the thickness of the fibrous substrate.

As shown in FIG. 7, the result of the method and apparatus of the present invention is a fibrous substrate 58 having particulate powder material 88 at selected areas 89 along the fibrous substrate 58. In a further step of fabricating a final hygenic article, the substrate 58 is cut along cut lines 90 to form individual fibrous pads 91. In addition, as shown in FIG. 8, the velocity of the first intermittent stream of particulate powder material applied to the substrate 58 is chosen such that a layer 92 of particlate powder material 88 forms within a predetermined portion of a thickness of each fibrous pad 91.

In accordance with current specifications for hygenic articles, the method and apparatus of the present invention allows the powder 88 to be centrally located and does not extend to the edges or ends of each individual pad 91. The width of powder material pattern 89 is determined by the length of the rectangular cross-section of outlet 42 of nozzle 38. The use of controller 82 to control the motion of nozzle 38 via a servomotor 84 permits "tuning" the discharge profile of particulate powder material and quickly changing the length of the pattern 89 by selecting an appropriate control program for controller 82. For example, if the servo velocity is constant over each product cycle the pattern length will be less than the length of pattern 89. On the other hand, if the servovelocity is increased near the beginning and end of each cycle, or the servovelocity is decreased at the middle of each cycle, this will result in a longer pattern than the length of pattern 89. The length of each individual pad 91 can be lengthened or shortened by adjusting the differential gear box 72. The length of an individual pad 91 is determined by the number of revolution that the maker drive shaft 56 makes for each product cycle. To lengthen or shorten the length of pattern 89, the gear box 72 is adjustable such that the encoder 78 turns one revolution over a wide range of revolutions of the maker drive shaft 56.

The present invention provides for a method and apparatus for applying an accurately metered quantity of particulate powder material to a moving fibrous substrate. In addition, the use of recycle means to recapture particulate powder material on the recycle side of the flow separator leads to a lower range of powder usage, translating to a lower raw material cost. Typically, the apparatus of the present invention utilizes an average flow of 0.15 grams of particulate powder material per product cycle.

While the invention has been particularly shown and described with respect to preferred embodiments thereof, it will be understood by those skilled in the art that the foregoing and other changes in form and details may be made therein without departing from the spirit and scope of the invention, which should be limited only by the scope of the appended claims.

What is claimed is:

1. An apparatus for applying particulate powder material to a substrate of fibrous material comprising:

conveyor means for supporting and moving said fibrous substrate in a horizontal path at a predetermined rate;

feeder means having an inlet means and an outlet means, wherein said inlet means receives said particulate powder material and said outlet means is connected to a continuously operating nozzle for producing a continuous stream of said particulate powder material; said nozzle being movable between a first position and a second position at a predetermined rate, said nozzle having an outlet for alternately directing said continuous stream of particulate powder material toward a predetermined location of said fibrous substrate and toward a diverter means; and said diverter means disposed above said conveyor means for intermittently receiving the continuous stream of particulate powder material from the nozzle to separate the stream into first and second intermittent streams of particulate powder material, whereby said first intermittent stream is applied to said fibrous substrate moving at said predetermined rate and at said predetermined location of said fibrous subsrate to form a layer of particulate powder material within a predetermined portion of said fibrous substrate.

2. The apparatus of claim 1 further comprising:

a source of supply for said particulate powder material, and transport means disposed above said feeder means for pneumatically transporting said particulate powder material from said source of supply to the inlet means of said feeder means.

3. The apparatus of claim 1 wherein said nozzle is positioned at an angel such that said continuous stream of particulate powder material exiting said nozzle has a velocity component which is in a direction of the moving fibrous subsrate.

4. The apparatus of claim 1 wherein said diverter means further comprises:

a wedge-shaped flow separator disposed beyond said nozzle outlet and intermediate of said first and second positions such that said continuous stream of particulate powder material is separated into said first and second intermittent streams each time the nozzle crosses a plane of the flow separator.

5. The apparatus of claim 1 wherein the nozzle comprises:

an inlet, a tapered outlet, a stationary pivot attached to said nozzle near said inlet, a movable shaft attached approximately midway of said nozzle, said inlet of said nozzle being connected to said outlet means of said feeder means for receiving said continuous stream of particulate powder material, said nozzle being movable by said movable shaft about said stationary pivot between a first position and a second position; and wherein said diverter comprises:

a wedge-shaped flow separator disposed beyond said outlet of said nozzle and intermediate of said first and second positions such that said continuous stream is separated into said first and second intermittent streams of particulate powder material each time the nozzle crosses a plane of the flow separator.

6. The apparatus of claim 5 wherein said diverter means further comprises control means for driving said nozzle between said first and second positions at a variable speed at said predetermined rate.

7. The apparatus of claim 6 wherein said control means comprises:

an encoder; and an adjustable differential gear box for driving said encoder such that said encoder revolves at said predetermined rate over a wide range of different speeds of a maker drive shaft.

8. The apparatus of claim 7 wherein said control means further comprises:

a servomotor connected to said movable shaft of said nozzle; and a programmable controller communicating with an output of said encoder and said servomotor for controlling the servovelocity of said servomotor such that said servomotor operates at a variable speed at said predetermined rate.

9. The apparatus of claim 6 wherein said control means comprises:

an adjustable differential gear box having a first shaft and a second shaft, said first shaft being connected to a maker drive shaft;

an encoder connected to said second shaft of said differential gear box wherein said differential gear box is operable to drive said encoder such that said encoder revolves at said predetermined rate over a wide range of different speeds of said maker drive shaft;

a servomotor connected to said movable shaft of said nozzle;

a programmable controller communicating with an output of said encoder and said servomotor for controlling the servovelocity of said servomotor such that said servomotor operates at a variable speed at said predetermined rate.

10. The apparatus of claim 1 wherein said feeder means comprises:

a feed hopper having a housing formed with an interior having an inlet and an outlet;

a feeder screw and a nozzle shroud mounted to said feed hopper, said feeder screw being rotatable to discharge metered quantities of particulate powder material from an interior portion of said housing through said outlet thereof;

a pump connected to said outlet of said housing, said pump transmitting a stream of air entrained particulate powder material through said outlet of said housing;

control means communicating with said transport means and a high and low sensor within said housing for maintaining the particulate powder material between the high and low sensors.

11. The apparatus of claim 1 further comprising recycle means for receiving said second intermittent stream of particulate powder material and pneumatically transporting said second stream of particulate powder material to said feeder means.

12. The apparatus of claim 11 wherein said recycle means comprises:

a flow separator having an inlet and an outlet, said inlet in intermittent communication with the nozzle to receive said second intermittent stream of a particulate powder material;

a pump connected to said outlet of said diverter block for forming a stream of air entrained particulate powder material and transporting said stream of air entrained particulate powder material form said diverter block;

a cyclone having a rotary air lock disposed above said feeder means and connected to said pump for receiving said stream of air entrained particlate powder material, wherein said cyclone separates said particlate powder material from said stream of air entrained particulate powder material and discharges said particlate powder material through said rotary air lock into said inlet of said feeder means.

13. The apparatus of claim 12 wherein the flow separator is wedge shaped.

* * * * *